United States Patent [19]

Kerb et al.

[11] Patent Number: 4,591,650
[45] Date of Patent: May 27, 1986

[54] HEXANOR-BRASSINOLID-22-ETHERS

[75] Inventors: Ulrich Kerb; Ulrich Eder; Hansjörg Krähmer, all of Berlin, Fed. Rep. of Germany

[73] Assignee: Schering Aktiengesellschaft, Berlin, Fed. Rep. of Germany

[21] Appl. No.: 579,856

[22] Filed: Feb. 13, 1984

[30] Foreign Application Priority Data

Feb. 17, 1983 [DE] Fed. Rep. of Germany ....... 3305747

[51] Int. Cl.$^4$ ........................................... C07D 313/10
[52] U.S. Cl. ..................................... 549/268; 71/88; 71/75; 71/77; 71/78; 71/76
[58] Field of Search ............................. 549/268; 71/88

Primary Examiner—Norma S. Milestone
Attorney, Agent, or Firm—Michael J. Striker

[57] ABSTRACT

New hexanor-brassinolid-22-ethers are disclosed, of the formula

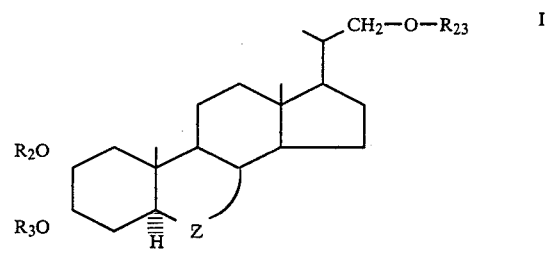

wherein Z is the group

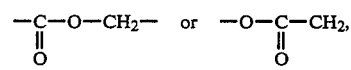

$OR_2$ and $OR_3$ are oriented cis $2\alpha$, $3\alpha$ or $2\beta$, $3\beta$, $R_2$ and $R_3$ are the same or different and are each hydrogen formyl, $C_2$–$C_7$-alkyl-CO—, $C_2$–$C_7$-alkoxy-$C_1$–$C_3$-alkyl-CO— or aryl-CO—, and $R_{23}$ is straight-chain or branched $C_1$–$C_7$-alkyl or $C_1$–$C_7$-alkoxy-$C_1$–$C_3$-alkyl. Also disclosed are processes for the production of these compounds as well as compositions containing the same having growth-regulatory activity for plants.

17 Claims, No Drawings

HEXANOR-BRASSINOLID-22-ETHERS

BACKGROUND OF THE INVENTION

The invention concerns new hexanor-brassinolid-22-ethers, processes for the production of these compounds, as well as compositions containing the same and having growth-regulatory activity for plants.

A plant growth promoting steroid, the brassinolid, has been isolated from the pollen of rape, and the structure has been determined (M. D. Grove et al., Nature, Vol. 281.216 (1979)). However, the growth-regulatory activity of this compound is not satisfactory.

Syntheses for this steroid are also known (J. Org. Chem. 44, 5002 (1979); Steroids 39, 89 (1982)). In these publications it is claimed that sterine side chains (with 8 to 10 carbon atoms), cis hydroxyl groups at $C_{22}$ and $C_{23}$, as well as alkyl groups at $C_{24}$ are essential for the brassino steroid activity.

SUMMARY OF THE INVENTION

It is therefore an object of the present invention to provide new brassinolid analogs which display outstanding plant growth-regulatory characteristics, however possess a simpler structure in comparison with the known analogous compounds, and are more easily prepared from a technical point of view.

This object is attained according to the present invention by a composition which is characterized by a content of a hexanor-brassinolid-22-ether of the Formula I

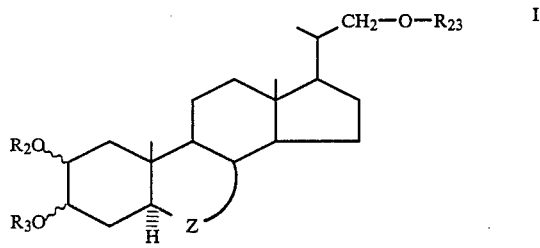

wherein
Z is the group

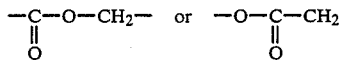

$OR_2$ and $OR_3$ are oriented cis $2\alpha$, $3\alpha$ or $2\beta$, $3\beta$, $R_2$ and $R_3$ are the same or different and are each hydrogen, formyl, $C_2$-$C_7$-alkyl-CO—, $C_2$-$C_7$-alkoxy-$C_1$-$C_3$-alkyl-CO— or aryl-CO— and $R_{23}$ is straight-chain or branched $C_1$-$C_7$-alkyl or $C_1$-$C_7$-alkoxy-$C_1$-$C_3$-alkyl.

By providing these new compounds, one succeeds in synthesizing, in surprising manner, simple structures with which, compared to the known brassinolid-derivatives, the three asymmetry centers ($C_{22}$, $C_{23}$, $C_{24}$) in the side chain are avoided, and therewith also the expensive separation of the diastereomers occurring with the syntheses at $C_{22}$ and $C_{23}$.

The compounds according to the present invention prove to be outstanding for the regulation of plant growth of various culture plants, and match the above mentioned products of the same activity direction in their activity spectra as well as in their compatibility.

The compounds according to the present invention make possible a promotion of the vegetative growth of culture plants, in certain concentration ranges, but also its restraint. In other respects it is possible to obtain certain multiple yields by means of influencing the generative phase.

In general, the substances work themselves into the membrane system of the culture plant, and alter its permeability for various substances.

Under certain conditions an anti-stress activity can be provided.

Since the compounds according to the present invention cause not only qualitative and quantitative alterations in the plants but also changes in metabolism, they are classified in the category of plant growth regulators, which distinguish through the following use possibilities:

Restraint of the vegetative growth of woody and weed plants, for example at road borders, railroad plants, and others, in order to prevent too voluptuous a growth. Growth restraint of grains, in order to eliminate depositing or breakage upon bending, with cotton for increasing the yield.

Influencing the branching of vegetative and generative organs of ornamental and culture plants, for increasing the onset of blooming, or with tobacco and tomato for restraining side shoots.

Improving the food quality, for example an increase in sugar content with sugar cane, sugar beets, or fruit, and a more uniform ripening of the harvested goods, which leads to higher yields.

Increasing the resistance against stress, thus for example against climatic influences, such as cold and dryness, but also against phytotoxic influence of chemicals.

Influencing the latex flow of rubber plants.

Formation of parthenocarpic fruit, pollen sterility and sexual influence are likewise use possibilities.

Control of the germination of seeds or the driving out of buds.

Defoliation or influencing the fruit fall in order to facilitate harvesting.

The compounds according to the present invention are suitable particularly for influencing the vegetative and generative growth of several legumes, such as for example soybeans and beta-beets.

The application amounts generally run between 0.001 and 1 kg active substance per hectare, indeed according to purpose of use, however if necessary also higher application amounts can be employed.

The time of use depends upon the purpose of use and the climatic conditions.

As substituents $R_2$ and $R_3$ according to the Formula I, mention may be made of acyl groups selected from formyl, the $C_2$-$C_7$-alkyl-CO-groups, the $C_2$-$C_7$-alkoxy-$C_1$-$C_3$-alkyl-CO-groups and the aryl-CO-groups, such as for example acetoxy, methoxyacetoxy, ethoxyacetoxy, propionyloxy, butyryloxy, valeryloxy, pentanoyloxy, hexanoyloxy, heptanoyloxy, dimethylacetoxy, diethylacetoxy, benzyloxy and phenylacetoxy.

As substituents $R_{23}$ mention may be made of methyl, ethyl, propyl, isopropyl, butyl, sec.-butyl, tert.-butyl, n-pentyl, n-hexyl and n-heptyl as $C_1$-$C_7$-alkyl groups, and of methoxymethyl, ethoxymethyl, propoxymethyl, methoxyethyl, among others, as $C_1$-$C_7$-alkoxy-$C_1$-$C_3$-alkyl groups.

The compounds according to the present invention can be used either alone, in mixture with one another, or with other active substances. If necessary, defoliation, plant protection or pest control agents can be added, indeed according to the desired purpose.

In so far as a broadening of the activity spectrum is desired, also other "biocides" can be added. For example, suitable as herbicidally effective mixing partners are those active substances that are set forth in Weed Abstracts, Vol. 31, 1981, under the title "Lists of common names and abbreviations employed for currently used herbicides and plant growth regulators in weed abstracts", which is hereby incorporated by reference. Moreover, also non-phytotoxic materials can be used, which can provide a synergistic increase in activity with herbicides and/or growth regulators, such as among others wetting agents, emulsifiers, solvents and oily additives.

Expediently the active substances according to the present invention or their mixtures can be applied in the form of preparations such as powders, spray agents, granulates, solutions, emulsions or suspensions, with the addition of liquid and/or solid carrier materials or diluting agents and, if necessary, wetting, adhering, emulsifying and/or dispersing aids.

Suitable liquid carrier substances include, for example, water, aliphatic and aromatic hydrocarbons such as benzene, toluene, xylene, cyclohexanone, isophorone, dimethylsulfoxide, dimethylformamide, and, moreover, mineral oil fractions.

Suitable solid carrier materials include, for example, mineral earths such as tonsil, silica gel, talc, kaolin, attaclay, limestone, silicic acid and plant products, such as meal.

As surface-active substances, mention may be made by way of example of calcium lignin sulfonate, polyoxyethylene-alkylphenolethers, naphthaline sulfonic acids and their salts, phenol sulfonic acids and their salts, formaldehyde condensate, fatty alcohol sulfate as well as substituted benzene sulfonic acids and their salts.

The portion of active substance or substances in the various preparations can range within broad limits. For example, the composition may contain about 10 to 80% by weight active substance, about 90 to 20% by weight liquid or solid carrier, as well as if necessary up to 20% by weight surface-active material.

The application of the composition can follow in customary manner, for example with water as carrier in spray brew amounts of about 100 to 1000 liter/ha. An employment of the composition in the so-called low-volume or ultra-low-volume techniques is likewise possible, as is their application in the form of so-called microgranulates.

For production of the preparations, the following components may be employed, by way of example:

A. SPRAY POWDER (a)

80% by weight active substance
15% by weight kaolin
5% by weight surface-active substance based upon the sodium salt of N-methyl-N-oleyl-taurine and the calcium salt of lignin sulfonic acid (b)

50% by weight active substance
40% by weight clay minerals
5% by weight cell pitch
5% by weight surface-active substance based upon a mixture of the calcium salt of lignin sulfonic acid with alkylphenolpolyglycolethers.

(c)

20% by weight active substance
70% by weight clay minerals
5% by weight cell pitch
5% by weight surface-active substance based upon a mixture of the calcium salt of lignin sulfonic acid with alkylphenolpolyglycolethers (d)

5% by weight active substance
80% by weight tonsil
10% by weight cell pitch
5% by weight surface-active substance based upon a fatty acid condensation product

B. EMULSION CONCENTRATE

20% by weight active substance
40% by weight xylene
35% by weight dimethylsulfoxide
5% by weight mixture of nonylphenylpolyoxyethylene or calcium dodecylbenzene sulfonate

C. PASTE

45% by weight active substance
5% by weight sodium aluminum silicate
15% by weight cetylpolyglycolether with 8 Mol ethylene oxide
2% by weight spindle oil
10% by weight polyethyleneglycol
23 parts water.

The new compounds according to the present invention can be produced, for example, by reacting compounds of the Formula

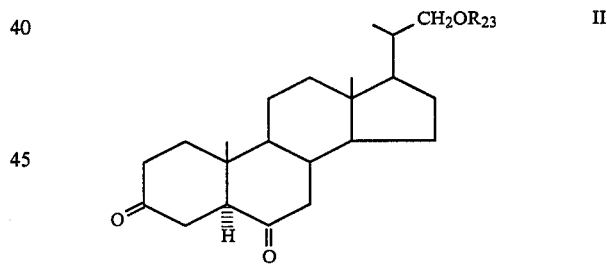

with chlorotrimethylsilane and zinc into compounds of the Formula

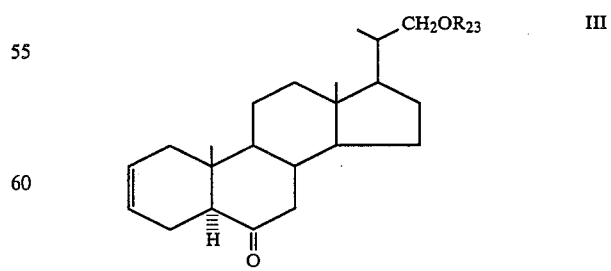

reacting the compounds of Formula III by osmium-tetroxide-catalyzed hydroxylation with t-butyl-hydroperoxide or with N-methyl-morpholin-N-oxide, into compounds of the Formula

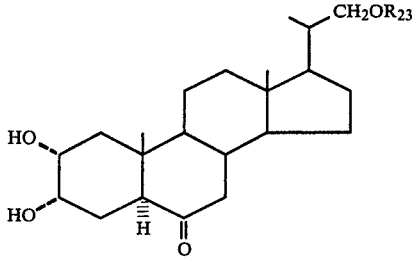

or with silver acetate and iodine in aqueous acetic acid to form compounds of the Formula

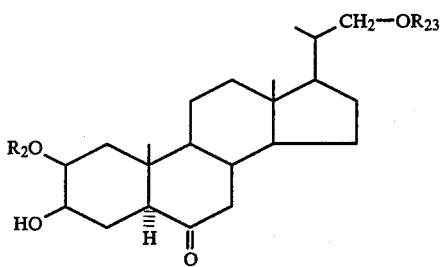

and then reacting the compounds of Formula IV or Formula V with peracids to form compounds of the Formula

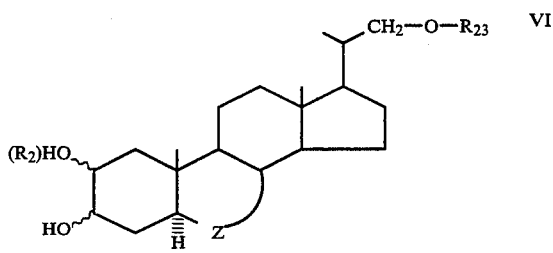

with or without then etherifying the 22-hydroxyl group by means of reacting of its 22-sulfonic acid-ester with an alkali alcoholate, wherein $R_2$ and $R_{23}$ have the above given meaning.

For representation of the compounds according to the present invention, one proceeds for example from 20-acetoxymethyl-5α-pregnane-3,6-dione of Formula II and reacts this in known manner with chlorotrimethylsilane and zinc into compounds of the Formula III.

The further reaction into 2α,3α-cis-glycols of Formula IV follows according to known methods, namely through the osmium tetroxide-catalyzed hydroxylation with 80% t-butylhydroperoxide or with N-methyl-morpholine-N-oxide.

One arrives at the 2β,3β-cis-glycols or their derivatives of Formula V by means of Prevost reaction with silver acetate and iodine in aqueous acetic acid.

The production of the B-ring lactone of Formula I follows through Baeyer-Villiger oxidation with peracids such as trifluoroperacetic acid, performic acid, permaleic acid of the 6-ketosteroids of Formulas IV and V.

The etherification of the 22-hydroxyl group follows in known manner through reaction of a 22-sulfonic acid ester with an alkali alcoholate. Beforehand in advantageous manner a protection of the 2,3-diol grouping, for example as acetonide, is necessary, a hydrolysis of the 22-acetate and reaction of the obtained 22-alcohol with a sulfonic acid chloride, such as methane sulfonic acid chloride, benzene sulfonic acid chloride or p-toluene sulfonic acid chloride being required.

In an alternative synthesis sequence, the etherification of compounds of Formula III can be performed, which is to be joined to the hydroxylation into the cis-glycols and thereafter the oxidation into the B-ring lactones of Formula I, which likewise form a part of the subject of the present invention.

The 2,3-alcohols of Formula I can be partially or completely esterified.

The novel features which are considered characteristic for the invention are set forth in particular in the appended claims. The invention itself, however, both as to its construction and its method of operation, together with additional objects and advantages thereof, will be best understood from the following description of specific embodiments.

DESCRIPTION OF THE PREFERRED EMBODIMENTS

EXAMPLE 1

(a) 20 g of 20S-acetoxymethyl-5α-pregnane-3,6-dione are dissolved in 200 ml tetrahydrofuran. 40 g zinc dust and 37.5 ml trimethylchlorosilane are added thereto and the mixture is heated at reflux for 1.5 hours under argon gasification. After cooling down, the mixture is sucked off by a vacuum, washed with tetrahydrofuran and methanol, and the filtrate is then compressed in a vacuum. After water precipitation, drying of the crude product and filtration over silica gel, it is recrystallized from ethanol-water. In this manner 11.5 g of 20S-acetoxymethyl-5α-pregn-2-ene-6-one are obtained.

MP: 77°–78° C.

(b) 8.4 g of 20S-acetoxymethyl-5α-pregn-2-en-6-one are dissolved in 50 ml tetrahydrofuran, reacted with 5 g N-methylmorpholin-N-oxide, 15 ml water and 20 ml t-butanol, and under stirring, a solution of 100 mg osmiumtetroxide in 15 ml tetrahydrofuran is added. The reaction solution is stirred for 21 hours at room temperature and under exclusion of light. Subsequently it is precipitated in sulfuric acid ice water, which was reacted with 500 mg sodium sulfide, the product is sucked off by vacuum, washed with water, withdrawn in methylene chloride, and evaporated in a vacuum. The crude product (8.6 g) is dissolved in 36 ml pyridine, and after addition of 18 ml acetanhydride and 860 g dimethylaminopyridine, left standing for 2 hours at room temperature. After water precipitation, sucking off of the product in a vacuum, washing with water and then drying, it is recrystallized from acetone-hexane. In this manner 6.1 g of 20S-acetoxymethyl-2α,3α-diacetoxy-5α-pregnane-6-one are obtained.

MP: 199°–200° C.

Through chromatography of the mother liquor, a further 2.2 g of the above compound are obtained, and 1.6 g 20S acetoxymethyl-2β,3β-diacetoxy-5α-pregnan-6-one.

MP: 142.5°–143.5° C.

(c) 7.5 ml of 30% hydrogen peroxide are suspended in 45 ml methylene chloride, cooled to −10° C., and slowly 46 ml trifluoroacetic acid anhydride are added dropwise, so that the interior temperature does not rise above +10° C. Subsequently, 7.8 g of 20S-acetoxymethyl-2α,3α-diacetoxy-5α-pregnan-6-one, dissolved in 40 ml methylene chloride, are added, followed by stirring for 75 minutes at room temperature. For further working up the product is diluted with methylene chloride and then washed with water and compressed in a vacuum. After chromatography on silica gel and recrystallization from acetone-hexane, one obtains 6.4 g 20S-acetoxymethyl-2α,3α-diacetoxy-B-homo-7-oxa-5α-pregnan-6-one, MP: 228.5°–230° C., and 650 mg of 20S-acetoxymethyl-2α,3α-diacetoxy-B-homo-6-oxa-5α-pregnane-7-one,

MP: 227.5°–229° C.

(d) 3.9 g of 20S-acetoxymethyl-2α,3α-diacetoxy-B-homo-7-oxa-5α-pregnane-6-one are dissolved in 40 ml methanol and 40 ml methylene chloride, and after addition of a solution of 2.5 g potassium hydroxide in 25 ml methanol, stirred for 40 minutes at 20° C. Thereafter the mixture is acidified with acetic acid, precipitated in ice water, after which the product is sucked off in a vacuum, washed with water and then dried. After recrystallization from methanol-methylene chloride, one obtains 2.7 g of 2α,3α-dihydroxy-20S-hydroxymethyl-B-homo-7-oxa-5α-pregnane-6-one.

MP: 242°–244° C.

(e) 1.4 g of 2α,3α-dihydroxy-20S-hydroxymethyl-B-homo-7-oxa-5α-pregnane-6-one are dissolved in 60 ml acetone, followed by an addition of 0.2 ml borotrifluoride-etherate, and then 90 minutes' stirring at 20° C. After an addition of 0.2 ml pyridine, the mixture is compressed in a vacuum, dissolved in ethyl acetate, washed with water and then evaporated. In this manner there are obtained 1.7 g amorphous 2α,3α-isopropylidenedioxy-20S-hydroxymethyl-B-homo-7-oxa-5α-pregnane-6-one.

1.4 g of the acetonide are dissolved in 6 ml pyridine, cooled to 0° C., reacted with 1 g p-toluene sulfonyl chloride, and then stirred for 3 hours at room temperature. After water precipitation, sucking off of the product in a vacuum, washing with water and then drying, it is recrystallized from ether. In this manner is obtained 2α,3α-isopropylidenedioxy-20S-toxyloxymethyl-B-homo-7-oxa-5α-pregnane-6-one.

MP: 146°–148° C.

(f) 500 mg 2α,3α-isopropylidenedioxy-20S-tosyloxymethyl-B-homo-7-oxa-5α-pregnane-6-one in 5 ml toluene are reacted with 1 g potassium propylate, dissolved in 2.5 ml dimethylsulfoxide, followed by stirring for 16 hours at room temperature. Thereafter the reaction mixture is cooled to 5° C., 3.5 ml of 36% perchloric acid are added, followed by stirring for 5 hours at 20° C. After working up and crystallization from ether, one obtains 385 mg 2α,3α-dihydroxy-20S-propoxymethyl-B-homo-7-oxa-5α-pregnane-6-one.

MP: 122°–124° C.

In analogous manner the following are produced:
2α,3α-dihydro-20S-ethoxymethyl-B-homo-7-oxa-5α-pregnane-6-one, MP: 125.5°–127.5° C.
2α,3α-dihydroxy-20S-(2'-methylpropyloxymethyl)-B-homo-7-oxa-5α-pregnane-6-one, MP: 135°–136° C.
2α,3α-dihydroxy-20S-(2',2'-dimethylpropyloxymethyl)-B-homo-7-oxa-5α-pregnane-6-one
2α,3α-dihydroxy-20S-(n-pentyloxymethyl)-B-homo-7-oxa-5α-pregnane-6-one.

EXAMPLE 2

(a) 1.3 g of 20S-acetoxy-2β,3β-diacetoxy-5α-pregnane-6-one are reacted with trifluoroperacetic acid, as described in Example 1(c). After working up, chromatography and recrystallization, one obtains 1.1 g 20S-acetoxy-methyl-2β,3β-diacetoxy-B-homo-7-oxa-5α-pregnane-6-one, MP: 212.5°–213.5° C., and 130 mg 20S-acetoxymethyl-2β,3β-diacetoxy-B-homo-6-oxa-5α-pregnane-7-one, MP: 190.5°–191.5° C.

(b) 1.1 g 20S-acetoxymethyl-2β,3β-diacetoxy-B-homo-7-oxa-5α-pregnane-6-one are reacted as described in Example 1(d)–(f). In this manner are obtained 280 mg 2β,3β-dihydroxy-20S-propyloxymethyl-B-homo-7-oxa-5α-pregnane-6-one, MP: 105°–108° C.

In analogous manner the following are produced:
2β,3β-dihydroxy-20S-methoxymethyl-B-homo-7-oxa-5α-pregnane-6-one, MP: 93°–95° C.
2β,3β-dihydroxy-20S-ethoxymethyl-B-homo-7-oxa-5α-pregnane-6-one
2β,3β-dihydroxy-20S-ethoxymethyl-B-homo-6-oxa-5α-pregnane-7-one.

EXAMPLE 3

(a) 22.6 g of 20S-acetoxymethyl-5α-pregn-2-en-6-one in 200 ml methylene chloride and 250 ml methanol are stirred with 2.5 g potassium hydroxide for 5 hours at room temperature and under argon atmosphere. The mixture is then neutralized with acetic acid, compressed and then precipitated in water. The product is sucked off in a vacuum, washed with water and then dried. Through recrystallization from methylene chloride/isopropylether there are obtained 18.3 g 20S-hydroxymethyl-5α-pregn-2-en-6-one, MP: 169.5°–170.5° C.

(b) 5 g 20S-hydroxymethyl-5α-pregn-2-en-6-one are reacted in 20 ml pyridine with 5 g p-toluene sulfonylchloride, and stirred for 3.5 hours at room temperature. Thereafter the mixture is precipitated in ice water, the product is sucked off in a vacuum, washed and then dried. Through recrystallization from ether-pentane, there are obtained 7 g 20S-tosyloxymethyl-5α-pregn-2-en-6-one.

MP: 156°–158° C.

(c) 5.4 g of the above tosylate are heated in 170 ml ethanol and 40 ml toluene with 4.5 g potassium ethylate, for 3 hours under reflux. After neutralization with acetic acid, the mixture is evaporated in a vacuum, withdrawn in acetic ester, washed with water and then evaporated. After recrystallization from methanol, one obtains 4.4 g 20S-ethoxymethyl-5α-pregn-2-en-6-one, MP: 64°–66° C.

(d) 4.4 g 20S-ethoxymethyl-5α-pregn-2-en-6-one are dissolved in 25 ml tetrahydrofuran, reacted with 2.5 g N-methylmorpholine-N-oxide, 7.5 ml water and 10 ml tert.-butanol, after which under stirring a solution of 50 mg osmium tetroxide in 15 ml tetrahydrofuran is added. The reaction solution is stirred 16 hours at room temperature. After working up and acetylation as in Example 1(b), one obtains after recrystallization from acetone/hexane 3.15 g 2α,3α-diacetoxy-20S-ethoxymethyl-5α-pregnan-6-one.

MP: 183°–184° C.

(e) 1.5 ml 30% hydrogen peroxide are suspended in 9 ml methylene chloride, cooled to −10° C., and 8.9 ml trifluoroacetic acid anhydride are slowly added dropwise, so that the interior temperature does not rise above +10° C. Subsequently there are added 1.5 g 2α,3α-diacetoxy-20S-ethoxymethyl-5α-pregnane-6-one, dissolved in 8 ml methylene chloride, followed by stirring for 1 hour at 22° C. After working up, chromatography and recrystallization from acetone/hexane, there are obtained 1.2 g 2α,3α-diacetoxy-20S-ethoxymethyl-B-homo-7-oxa-5α-pregnane-6-one, MP: 189.5°–191° C., and 150 mg 2α,3α-diacetoxy-20S-ethoxymethyl-B-homo-6-oxa-5α-pregnane-7-one, MP: 198°–200° C.

(f) 890 mg 2α,3α-diacetoxy-20S-ethoxymethyl-B-homo-7-oxa-5α-pregnane-6-one in 15 ml methanol are stirred for 20 minutes at 20° C. with 500 mg potassium hydroxide, and then further worked up. After recrystallization from ether/pentane, one obtains 695 mg 2α,3α-dihydroxy-20S-ethoxymethyl-B-homo-7-oxa-5α-pregnane-6-one, MP: 128°–130° C.

In analogous manner the following are produced:

2α,3α-dihydroxy-20S-methoxymethyl-B-homo-7-oxa-5α-pregnane-6-one, MP: 151°–152° C.

2α,3α-dihydroxy-20S-ethoxymethyl-B-homo-6-oxa-5α-pregnane-7-one, MP: 136°–137° C.

2α,3α-dihydroxy-20S-butoxymethyl-B-homo-7-oxa-5α-pregnane-6-one

2α,3α-dihydroxy-20S-2',2'-dimethylpropoxymethyl-B-homo-7-oxa-5α-pregnane-6-one

2α,3α-dihydroxy-20S-methoxyethoxymethyl-B-homo-7-oxa-5α-pregnane-6-one, MP: 46°–48° C.

2α,3α-dihydroxy-20S-propoxyethoxymethyl-B-homo-7-oxa-5α-pregnane-6-one

2α,3α-dihydroxy-20S-methoxyethoxymethyl-B-homo-6-oxa-5α-pregnane-7-one

2α,3α-dihydroxy-20S-butoxyethoxymethyl-B-homo-7-oxa-5α-pregnane-6-one.

EXAMPLE 4

2 g 2α,3α-dihydroxy-20S-methoxymethyl-B-homo-7-oxa-5α-pregnane-6-one are dissolved in 20 ml pyridine, cooled to 0° C. and then reacted with 2 ml acetic anhydride. The reaction mixture is then stirred for 5 hours at 0°–5° C., cast into ice water, sucked off in a vacuum, washed and then dried. After recrystallization from acetone/hexane there are obtained 1.6 g 2α-acetoxy-3α-hydroxy-20S-methoxymethyl-B-homo-7-oxa-5α-pregnane-6-one.

MP: 121°–122° C.

In analogous manner, the following are prepared:

2α-acetoxy-3α-hydroxy-20S-ethoxymethyl-B-homo-7-oxa-5α-pregnane-6-one, MP: 92°–93.5° C.

2α-acetoxy-3α-hydroxy-20S-methoxyethoxymethyl-B-homo-7-oxa-5α-pregnane-6-one, an amorphous substance 3β-acetoxy-2β-hydroxy-20S-ethoxymethyl-B-homo-7-oxa-5α-pregnane-6-one, MP: 97°–98° C.

2α-acetoxy-3α-hydroxy-20S-ethoxymethyl-B-homo-6-oxa-5α-pregnane-7-one, MP: 111°–112.5° C.

The compounds according to the present invention represent as a rule crystalline colorless and odorless substances which are difficultly soluble in water, conditionally soluble in aliphatic hydrocarbons such as petroleum ether, hexane, pentane and cyclohexane, well soluble in halogenated hydrocarbons such as chloroform, methylene chloride, carbon tetrachloride, aromatic hydrocarbons such as benzene, toluene and xylene, ethers such as diethylether, tetrahydrofuran and dioxane, carboxylic acid nitriles such as acetonitrile, ketones such as acetone, alcohols such as methanol and ethanol, carboxylic acid amides such as dimethylformamide, and sulfoxides such as dimethylsulfoxide.

The next Examples illustrate the use possibilities of the compounds according to the present invention, and follow in the form of the above-given preparations.

EXAMPLE 5

Soybeans are soaked with the compounds according to the present invention dissolved in a solvent, in an amount of 50 g active substance per 100 kg seed goods.

For germination, the seeds are placed in glass tumblers with 3 ml water. After 7 days cultivation at 25° C., the following symptoms are evaluated:

shortening and thickening of the hypocotyls, twisting of the hypocotyl necks, reduction of the root layout.

The evaluation follows by classification according to the scheme 0–4, whereby 0 = no activity and 4 = strongest activity.

| Compounds according to the Invention | Evaluation of Symptoms |
|---|---|
| 2α,3α-dihydroxy-20S—ethyoxymethyl-B—homo-7-oxa-5α-pregnane-6-one | 4 |
| 2α,3α-dihydroxy-20S—(2'-methylpropyloxymethyl)-B—homo-7-oxa-5-pregnane-6-one | 4 |
| 2α,3α-dihydroxy-20S—methoxymethyl-B—homo-7-oxa-5α-pregnane-6-one | 3 |
| 2α,3α-dihydroxy-20S—methoxyethoxy-methyl-B—homo-7-oxa-5α-pregnane-6-one | 2 |
| Control | 0 |

EXAMPLE 6

Beta-beets are placed in a greenhouse and treated in a hydro-culture vessel with 5 and 10 ppm of the active substance, provided as a powdery preparation. After 10 days, the lengthening of the leaves and the beet diameters are determined in comparison to the control. The leaves following the cotyledons are considered.

| Compounds According to the Invention | ppm active substance | Percent Lengthening of the Leaves | | | Percent Beet Diameter |
|---|---|---|---|---|---|
| | | 5 | 6 | 7 | |
| 2α,3α-dihydroxy-20S—ethoxymethyl-B—homo-7-oxa-5α-pregnane-6-one | 5 | 162 | 141 | 383 | 142 |
| | 10 | 121 | 100 | 383 | 145 |
| 2α,3α-dihydroxy-20S—propoxymethyl-B—homo-7-oxa-5α-pregnane-6-one | 5 | 102 | 102 | 233 | 115 |
| | 10 | 114 | 105 | 317 | 115 |

The findings show that the substances according to the present invention lead to an intense stimulation of the vegetative growth of the beets, which signifies an increase in yield.

EXAMPLE 7

The test substances are applied, dissolved in an acetone-containing lanolin oil, to Pinto beans. The application was done after the second internodes had obtained a length of 2 mm. Application amounts of 10, 50 and 100 μg active substance were employed. The evaluation was performed after three days.

In the following Table the percent lengthenings and the classification numbers for the internode growth are set forth. The classification numbers refer to the degree of bending and thickening of the internodes (from 0 to 5).

| Compounds According to the Invention | 100 μg | 50 μg | 10 μg |
|---|---|---|---|
| 2α,3α-dihydroxy-20S—ethoxymethyl-B—homo-7-oxa-5-pregnane-6-one | 20 (4) | 131 (4) | 39 (1) |
| 2α,3α-dihydroxy-20S—(2'-methylpropyloxymethyl)- | 39 (4) | 25 (3) | 0 |

-continued

| Compounds According to the Invention | 100 μg | 50 μg | 10 μg |
|---|---|---|---|
| B—homo-7-oxa-5-pregnane-6-one | | | |

The findings prove that the compounds according to the present invention cause an intensive stimulation of the vegetative growth.

It will be understood that each of the elements described above, or two or more together, may also find a useful application in other types of growth-regulating compounds differing from the types described above.

While the invention has been illustrated and described as embodied in hexanor-brassinolid-22-ethers, processes for the production of these compounds, as well as compositions containing the same having growth regulatory activity for plants, it is not intended to be limited to the exemplary details, since various modifications may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. 2α,3α-di-hydroxy-20S-propoxymethyl-B-homo-7-oxa-5α-pregnane-6-one.
2. 2α,3α-dihydroxy-20S-ethoxymethyl-B-homo-7-oxa-5α-pregnane-6-one.
3. 2α,3α-dihydroxy-20S-(2'-methylpropyloxymethyl)-B-homo-7-oxa-5α-pregnane-6-one.
4. 2α,3α-dihydroxy-20S-(2',2'-dimethylpropyloxymethyl)-B-homo-7-oxa-5α-pregnane-6-one.
5. 2α,3α-dihydroxy-20S-(n-pentyloxymethyl)-B-homo-7-oxa-5α-pregnane-6-one.
6. 2β,3β-dihydroxy-20S-propyloxymethyl-B-homo-7-oxa-5α-pregnane-6-one.
7. 2β,3β-dihydroxy-20S-methoxymethyl-B-homo-7-oxa-5α-pregnane-6-one.
8. 2β,3β-dihydroxy-20S-ethoxymethyl-B-homo-7-oxa-5α-pregnane-6-one.
9. 2α,3α-dihydroxy-20S-methoxymethyl-B-homo-7-oxa-5α-pregnane-6-one.
10. 2α,3α-dihydroxy-20S-butoxymethyl-B-homo-7-oxa-5α-pregnane-6-one.
11. 2α,3α-dihydroxy-20S-methoxyethoxymethyl-B-homo-7-oxa-5α-pregnane-6-one.
12. 2α,3α-dihydroxy-20S-propoxyethoxymethyl-B-homo-7-oxa-5α-pregnane-6-one.
13. 2α,3α-dihydroxy-20S-butoxyethoxymethyl-B-homo-7-oxa-5α-pregnane-6-one.
14. 2α-acetoxy-3α-hydroxy-20S-methoxymethyl-B-homo-7-oxa-5α-pregnane-6-one.
15. 2α-acetoxy-3α-hydroxy-20S-ethoxymethyl-B-homo-7-oxa-5α-pregnane-6-one.
16. 2α-acetoxy-3α-hydroxy-20S-methoxyethoxymethyl-B-homo-7-oxa-5α-pregnane-6-one.
17. 3β-acetoxy-2β-hydroxy-20S-ethoxymethyl-B-homo-7-oxa-5α-pregnane-6-one.

* * * * *